(12) United States Patent
Goodin et al.

(10) Patent No.: US 6,361,529 B1
(45) Date of Patent: **\*Mar. 26, 2002**

(54) STIFFENING MEMBER IN A RAPID EXCHANGE DILATION CATHETER

(75) Inventors: Rich L. Goodin, Blaine; Suranjan Roychowdhury, Minneapolis; Katherine Prindle, Robbinsdale, all of MN (US)

(73) Assignee: Schneider (USA) Inc., Maple Grove, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/576,782

(22) Filed: May 23, 2000

Related U.S. Application Data

(63) Continuation of application No. 09/150,463, filed on Sep. 9, 1998, now Pat. No. 6,066,114.

(51) Int. Cl.$^7$ .............................................. A61M 25/00
(52) U.S. Cl. ............... 604/524; 604/102.02; 604/96.01; 606/194
(58) Field of Search ...................... 604/96.01, 102.01, 604/102.02, 103, 523, 524; 606/192, 194

(56) References Cited

U.S. PATENT DOCUMENTS

| | | | |
|---|---|---|---|
| 4,137,906 A | 2/1979 | Akiyama et al. | |
| 4,748,982 A | 6/1988 | Horzewski et al. | |
| 4,762,129 A | 8/1988 | Bonzel | |
| 4,943,278 A | 7/1990 | Euteneuer et al. | |
| B1 4,762,129 | 7/1991 | Bonzel | |
| 5,154,725 A | 10/1992 | Leopold | |
| 5,156,594 A | 10/1992 | Keith | |
| 5,328,472 A | 7/1994 | Steinke et al. | |
| 5,413,559 A | 5/1995 | Sirhan et al. | |
| 5,489,271 A | 2/1996 | Andersen | |
| 5,549,557 A | 8/1996 | Steinke et al. | |
| 5,605,543 A | 2/1997 | Swanson | |
| 5,607,394 A | 3/1997 | Andersen et al. | |
| 5,634,902 A | 6/1997 | Johnson et al. | |
| 5,658,251 A | 8/1997 | Ressemann et al. | ... 604/102.01 |
| 5,728,067 A | 3/1998 | Enger | |
| 5,882,336 A | 3/1999 | Janacek | |
| 5,921,958 A | 7/1999 | Ressemann et al. | ..... 604/96.01 |
| 6,066,114 A | 5/2000 | Goodin et al. | |

FOREIGN PATENT DOCUMENTS

| | | |
|---|---|---|
| WO | 92/17236 | 10/1992 |

*Primary Examiner*—Richard K. Seidel
*Assistant Examiner*—Jeremy Thissell
(74) *Attorney, Agent, or Firm*—Scimed Life Systems, Inc.

(57) ABSTRACT

A dilation catheter having a first shaft section, a second shaft section attached to the first shaft section, and an inflatable balloon attached to the second shaft section. A fluid pathway is defined through the catheter for inflation of the balloon. A guide wire lumen is provided in the second shaft section that can extend between the distal end of the balloon and a point distal of the first shaft section. A stiffening member is provided within the second shaft section of the dilation catheter to provide additional stiffness to the second shaft section. In a preferred embodiment, the stiffening member is attached at the distal end of the first shaft section to occlude the hollow passage of the first shaft section. In this embodiment, the first shaft section farther includes a fluid port that is proximal of the stiffening member and that extends between the hollow passage of the first shaft section and the exterior of the first shaft section. The second shaft section overlaps the first shaft section so that the hollow passage of the second shaft section is in fluid communication with the fluid port of the first shaft section to define the fluid flow pathway. The stiffening member is free from fixed interconnection at its distal end, and includes a linear tapered region along a portion of its length to provide a gradient of stiffness to the second shaft section along the length of the stiffening member.

6 Claims, 2 Drawing Sheets

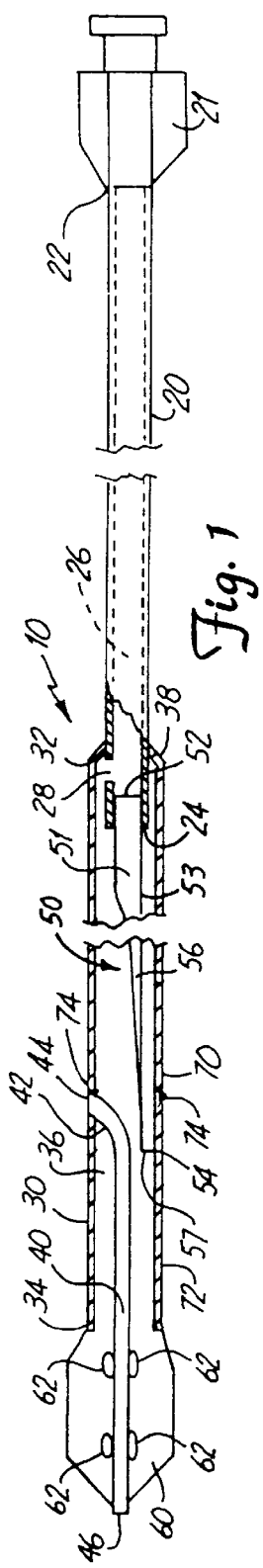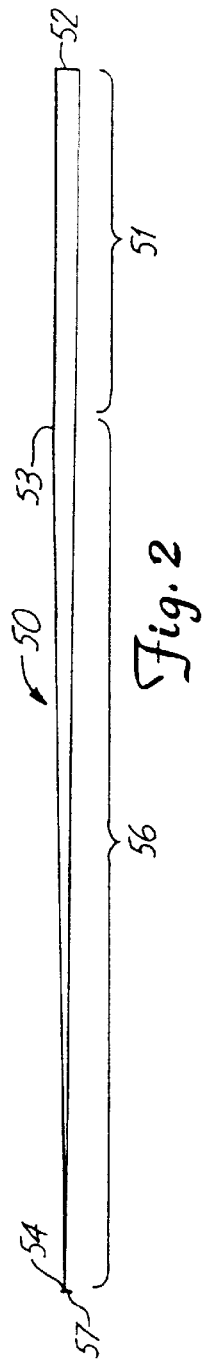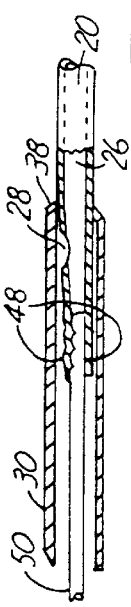

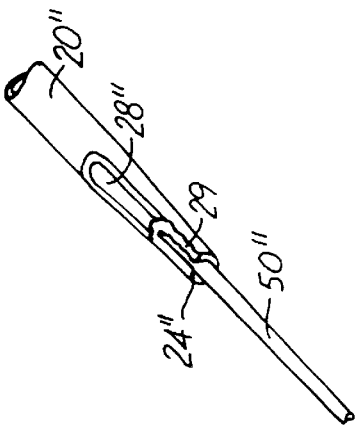
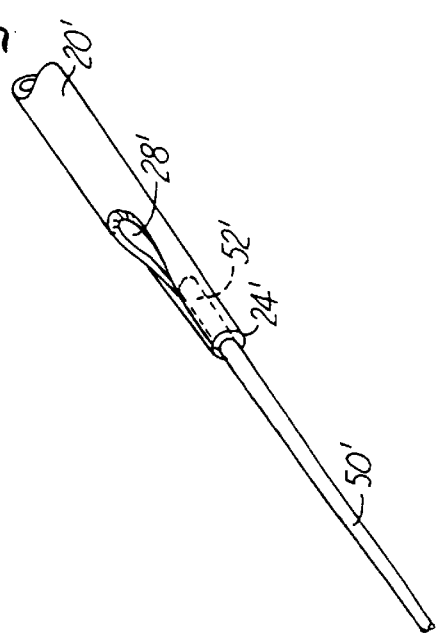
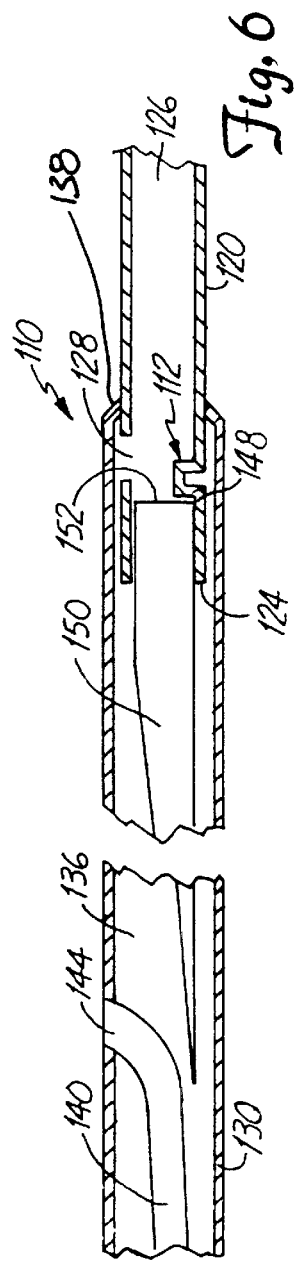
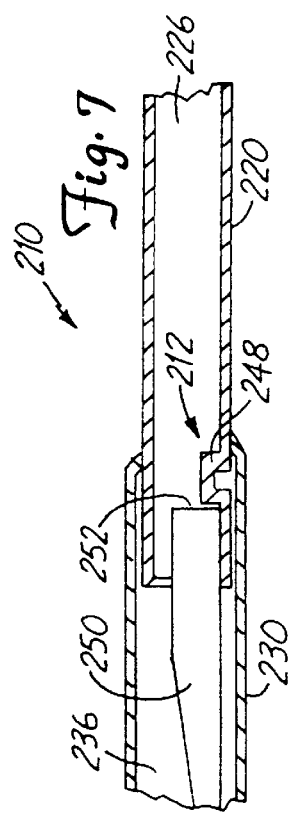

STIFFENING MEMBER IN A RAPID EXCHANGE DILATION CATHETER

REFERENCE TO RELATED APPLICATION

This application is a continuation of application Ser. No. 09/150,463 filed on Sep. 9, 1998, now U.S. Pat. No. 6,066, 114, and which is hereby incorporated by reference in its entirety.

TECHNICAL FIELD

The present invention relates generally to medical devices for insertion and advancement through a body lumen. In particular, the present invention is a balloon catheter having a stiffening member for use in intravascular catheterization therapies.

BACKGROUND OF THE INVENTION

Intravascular catheters are presently in wide clinical use for a variety of diagnostic and therapeutic purposes. Intravascular catheterization therapies, such as percutaneous transluminal coronary angioplasty ("PTCA"), have been developed as alternatives to bypass surgery for treating vascular diseases or other conditions that occlude or reduce the lumen size of portions of a patient's vascular system. In particular, balloon angioplasty has proven to be a useful, and in many circumstances preferred, treatment for obstructive coronary diseases.

In a typical PTCA procedure, a guide catheter is introduced into a peripheral artery of a patient, such as a femoral artery through an incision at the groin. The guide catheter is advanced through the femoral or other peripheral artery to a desired coronary site. Typically, the guide catheter is advanced through the aorta until the distal end of the guide catheter is positioned adjacent to the coronary ostium for the coronary artery to be treated. A guide wire is introduced through the guide catheter, and a balloon dilation catheter is then introduced over the guide wire. More particularly, the guide wire is advanced past the distal end of the guide catheter within the lumen of the diseased vessel and manipulated across the region of stenosis. The balloon dilation catheter is then advanced past the distal end of the guide catheter over the guide wire until the balloon is positioned across the region of stenosis. The balloon is then inflated by supplying a fluid under pressure to the balloon through an inflation lumen in the balloon dilation catheter, which stretches the diseased vessel to re-establish acceptable blood flow through the vessel. Intravascular therapeutic and diagnostic procedures utilizing dilation catheters, such as PTCA, have achieved wide acceptance because of their effectiveness and because they involve a relatively minor surgical procedure as compared to coronary bypass surgery.

Advancing a catheter to position a balloon across a stenotic lesion can be a difficult and time consuming task due to the tortuous passages through which the catheter must be navigated by a physician. The efficacy of such procedures relies upon the balloon being precisely positioned at the desired location. Furthermore, catheters must be able to traverse tortuous pathways in a patient's vasculature in a manner as atraumatic to the patient as possible. To satisfy these requirements, catheters must balance a number of competing design criteria. Specifically, catheters should have a small profile to permit navigation through small body lumens. The catheter must be axially strong along its longitudinal length to give the catheter "pushability" for transmitting a longitudinal force along the catheter so a physician can push the catheter through the vascular system to the stenosis. At the same time, however, the catheter must be flexible so that the catheter has good "trackability" so as to be able to navigate the tortuous passages of a patient's vascular system.

To satisfy these competing design criteria, catheters typically have a stiff proximal portion and a flexible distal portion to which the inflation balloon is attached. The stiff proximal portion gives the catheter sufficient axial and longitudinal strength to give the catheter pushability, while the flexible distal portion permits the catheter to pass through tortuous, tight curvatures of the vasculature.

One type of balloon dilation catheter, commonly referred to as an "over-the-wire" catheter, typically includes a single lumen shaft that extends from the proximal end of the catheter to the distal end of the balloon. A guide wire is inserted into and extends along the length of the single lumen shaft. The guide wire is used to steer the catheter through the patient's vasculature by advancing the catheter over the previously inserted wire until the balloon is positioned at a desired treatment location. In this catheter, the guide wire must be inserted into and through the entire length of the dilation catheter prior to the catheter being inserted into a patient's vasculature. As such, the guide wire must protrude from the patient's body by a length greater than the length of the dilation catheter. Moreover, because the guide wire extends through the length of the catheter there is relatively large friction between the guide wire and the catheter. As a result, manipulation of an over-the-wire dilation catheter can be difficult.

A catheter design that alleviates these shortcomings is referred to as a "rapid-exchange" catheter. An example of a rapid-exchange catheter is described in United States Patent Reexamination Certificate B1 4,762,129 to Bonzel, the entire disclosure of which is hereby incorporated by reference for all purposes.

While catheters of the rapid-exchange type have been highly successful in PTCA procedures, the flexible distal portion of such catheters may kink and/or buckle when the catheter is subjected to high axial loads. A region of the catheter where such kinking and buckling can occur is the interface between the stiff proximal portion and the flexible distal portion of the catheter due to the change in stiffness at this interface. Attempts have been made to provide a structure that resists kinking and buckling in this region. Such structures are described in U.S. Pat. No. 5,156,594 to Keith, U.S. Pat. No. 5,658,251 to Ressemann et al, and U.S. Pat. No. 4,748,982 to Horzewski et al.

There is a continuing need for improved catheters, however. In particular, a rapid-exchange catheter having a stiffening member that provides a gradually varying stiffness at the interface between a stiff proximal portion and a flexible distal portion of the catheter is highly desirable. Such a stiffening member should be efficient to manufacture and use, and should be effective in providing sufficient stiffness to the interface between the proximal and distal portions of the catheter, while not unduly influencing the flexibility of the catheter.

SUMMARY OF THE INVENTION

The present invention is a dilation catheter for insertion into and advancement through a body lumen. In a first embodiment, the dilation catheter comprises a first shaft section having a proximal end, a distal end, and a first stiffness. The first shaft section also includes a hollow passage along a length of the first shaft section and a fluid port proximal of the distal end of the first shaft section. The fluid port extends between the hollow passage and the exterior surface of the first shaft section. In this manner the hollow passage and the fluid port permit fluid flow through a length of the first shaft section. A second shaft section has a proximal end which is attached to the first shaft section at a region adjacent the distal end of the first shaft section. The second shaft section further includes a distal portion and has a second stiffness that is less than the first stiffness of the first shaft section. The second shaft section includes a hollow passage along a length of the second shaft section that is in fluid communication with the fluid port of the first passage to define a fluid pathway between the length of the first shaft section and the length of the second shaft section. A dilation member is attached to the distal portion of the second shaft section and is fluidly coupled to the hollow passage of the length of the second shaft section. In this manner, the dilation member receives fluid.

The dilation catheter further includes a guide wire lumen in at least a portion of the second shaft section. The guide wire lumen includes a proximal end that extends through the second shaft section at a location distal of the first shaft section. The guide wire lumen permits the insertion of a guide wire into the lumen. A stiffening member is further provided in the dilation catheter. The stiffening member includes a proximal end that is attached to the distal end of the first shaft section so as to occlude the hollow passage of the first shaft section at a location distal of the first shaft section fluid port. The stiffening member extends into the hollow passage of the second shaft section to provide additional stiffness to the second shaft section of the dilation catheter at a region along the length of the stiffening member. The stiffening member preferably includes a tapered region having a gradient of stiffness along its length to provide a gradient of stiffness to the second shaft section.

In a second embodiment, the stiffening member of the dilation catheter is a "floating" member that is free from fixed interconnection with the first shaft section and the second shaft section. The first shaft section includes the features of the first shaft section of the first embodiment described above, and further includes an axial stop member that projects into the hollow passage of the length of the first shaft section to arrest the axial motion of the stiffening member in the proximal direction as the catheter is advanced in the body lumen. The stiffening member can have substantially the same cross sectional shape and area as the hollow passage of the length of the first shaft section to occlude the hollow passage when it engages the axial stop member. In this embodiment, the fluid pathway is defined by the hollow passage and fluid port of the first shaft section, and by the hollow passage of the length of the second shaft section.

In a third embodiment of the present invention, a balloon dilation catheter can include a stiffening member that has a cross sectional area that is less than the cross sectional area of the hollow passage of a first shaft section. In such an embodiment, the fluid flow pathway through the dilation catheter is preferably substantially linear between the first and second shaft sections, and the first shaft section need not include a fluid port.

BRIEF DESCRIPTION OF THE DRAWINGS

FIG. 1 is a side view of a dilation catheter in accordance with the present invention shown partially in section to illustrate a stiffening member in a second shaft section for providing additional stiffness to the second shaft section as the catheter is advanced in a body lumen.

FIG. 2 is a side view of the stiffening member of the dilation catheter of FIG. 1.

FIG. 3 is a detailed side view of a portion of the catheter of FIG. 1 shown in section to illustrate a first structure for attachment of the stiffening member to the first shaft section.

FIG. 4 is an isometric view of a portion of a first shaft section and a stiffening member in accordance with the present invention showing a second structure for attaching the stiffening member to the first shaft section.

FIG. 5 is an isometric view of a portion of a first shaft section and a stiffening member in accordance with the present invention showing a third structure for attaching the stiffening member to the first shaft section.

FIG. 6 is a sectional view of a portion of a second embodiment of a dilation catheter in accordance with the present invention shown in section to illustrate a floating stiffening member in a second shaft section that is free from fixed attachment to a first shaft section.

FIG. 7 is a side sectional view of a portion of a third embodiment of a dilation catheter in accordance with the present invention having a floating stiffening member.

DETAILED DESCRIPTION OF THE PREFERRED EMBODIMENTS

With reference to the Figures, and more specifically to FIGS. 1–3, a dilation catheter 10 in accordance with the present invention is shown. Dilation catheter 10 is comprised of a first shaft section 20, a second shaft section 30 that is attached to the first shaft section, such as hypotube 20, and a dilation member, such as inflatable balloon 60, attached to the second shaft section 30. Dilation catheter 10 is adapted to be inserted into and advanced through a body lumen to position balloon 60 at a desired treatment site within a patient. Balloon 60 receives a fluid flow through catheter 10 for inflation of balloon 60 when positioned at the desired treatment location. In this manner, dilation catheter 10 can be used to treat arterial and coronary diseases by re-establishing acceptable blood flow through a partially occluded body lumen in a patient's vasculature.

Hypotube 20 of dilation catheter 10 includes a proximal end 22 and a distal end 24. Proximal end 22 is attached to a hub 21 in a conventional manner. Hypotube 20 includes a hollow passage, such as lumen 26 (shown partially in phantom), along its length that is fluidly coupled to hub 21. Hub 21 can be attached to an external source of fluid flow (not shown) to permit fluid flow into lumen 26 of hypotube 20.

The second shaft section 30 includes a proximal end 32 that is attached to hypotube 20 at a region adjacent to the distal end 24. Second shaft section 30 also includes a hollow passage, such as lumen 36, along its length that is in fluid communication with the lumen 26 of the hypotube 20. A distal end 34 of second shaft section 30 is sealingly attached to balloon 60 in such a manner that the lumen 36 of second shaft section 30 is fluidly coupled to balloon 60. In this manner, balloon 60 can receive fluid through the catheter 10 for inflation of the balloon 60 at the desired treatment site within a patient's vasculature.

In order to provide pushability to dilation catheter 10, a hypotube 20 is preferably used as the first shaft section in a known manner. Hypotube 20 is an elongated, thin walled metal tube, typically constructed of stainless steel, having lumen 26 along its length. Because of its thin walled construction, hypotube 20 provides a small diameter shaft section to permit passage of catheter 10 through a small body lumen. The use of stainless steel for hypotube 20 provides sufficient axial strength to deliver pushability to catheter 10. Hypotube 20 is also sufficiently flexible along its length due to its thin walled construction to permit navigation of dilation catheter 10 through arteries in a patient's vasculature, such as the less tortuous regions of the femoral artery or the like. Other structures that provide the desired combination of flexibility and pushability can, of course, also be used.

Second shaft section 30 is preferably constructed of a polymeric material so as to have a stiffness that is less than the stiffness of the hypotube 20. In this manner, flexible shaft section 30 improves the trackability of dilation catheter 10. Proximal end 32 of second shaft section 30 overlaps and is attached to the hypotube 20 at a location that is adjacent the distal end 24. Lumen 36 of the second shaft section 30 thus preferably has a cross sectional area that is greater than the cross sectional area of the hypotube 20. In the embodiment shown, second shaft section 30 and hypotube 20 both have a circular cross sectional shape, although other shapes can, of course, be used. The second shaft section 30 thus preferably has an inner diameter (i.e. the diameter of lumen 36) that is greater than the outer diameter of hypotube 20. Proximal end 32 of second shaft section 30 is positioned over the distal end 24 so as to overlap a region of hypotube 20 adjacent distal end 24, and a seal 38 is created between the second shaft section 30 and the hypotube 20 at proximal end 32 in a conventional manner, such as by heat shrinking the polymeric second shaft section 30 to hypotube 20 or using adhesive to secure the second shaft section 30 to the hypotube 20.

In the embodiment shown, dilation catheter 10 is a rapid exchange catheter, and thus includes a guide wire lumen 40 in the second shaft section 30 to permit the insertion of a guide wire (not shown). The guide wire lumen 40 terminates at its proximal end 42 in a skive 44 positioned between the balloon 60 and the distal end 24 of the hypotube 20. In this manner, guide wire lumen 40 is positioned only in the second shaft section 30, and the guide wire thus does not have to extend as far out of a patient's lumen to permit the insertion of the catheter 10 over the guide wire. This, in turn, permits more rapid exchange between different catheters if necessary during a medical procedure, and reduces the frictional resistance between the guide wire and the dilation catheter 10 as compared to conventional, over-the-wire catheters.

The guide wire lumen 40 extends through the balloon 60 and terminates in a tip 46 at its distal end. In use, a guide wire is inserted into lumen 40 through tip 46 and exits skive 44 of lumen 40. The guide wire provides a support structure for directing catheter 10 to the desired treatment location in a patient's vasculature. To aid in navigation of the vasculature, radiopaque markers 62 are attached to the guide wire lumen 40 to permit the position of catheter 10 to be tracked radiographically during the insertion and advancement of catheter 10 in the body lumen. The use of markers 62 is generally known. The markers 62 can be positioned at any known location in balloon 60, such as at the mid point of the balloon 60, or symmetric with the mid-point of balloon 60. Markers 62 thus provide a precise indication of the position of the balloon 60 in a patient's lumen.

As perhaps best shown in FIG. 1, the second shaft section 30 can be comprised of a proximal portion 70 and a distal portion 72. Proximal portion 70 can be formed from a polymeric material having a greater stiffness than the distal portion 72. In this manner, the second shaft section 30 can have a varying degree of stiffness to provide for better trackability of catheter 10, thus aiding in navigation through the body lumen. Proximal portion 70 and distal portion 72 can be attached at a butt joint 74 using conventional methods, such as heat sealing or adhesive. A convenient location for butt joint 74 is at the point where skive 44 of guide wire lumen 40 extends from the second shaft section 30. Other methods for interconnecting proximal portion 70 and distal portion 72 can of course be used, and the location for the interconnection can vary along the length of second shaft section 30 as desired. Moreover, second shaft section 30 can be comprised of additional, separately formed portions having different stiffnesses to create a desired stiffness profile along the length of second shaft section 30.

Dilation catheter 10 also includes a stiffening member 50 that provides additional stiffness to the second shaft section 30 along the length of the stiffening member 50. As described above, the hypotube 20 of catheter 10 is preferably formed from a relatively stiff material such as thin walled stainless steel, while the second shaft section 30 is formed from a more flexible, polymeric material. Such a construction balances the competing design criteria associated with catheters, namely providing axial strength and pushability while being sufficiently flexible to navigate tortuous body lumens.

As described in the Background section, known catheters can be susceptible to buckling and kinking at the interface between a stiff proximal section, such as hypotube 20, and a more flexible distal portion, such as second shaft section 30, as a guide wire is inserted in the catheter or as the catheter is advanced in a body lumen. This is primarily due to the abrupt change in stiffness at the interface between the hypotube 20 and the second shaft section 30. To reduce the incidence of buckling or kinking, dilation catheter 10 includes stiffening member 50 that provides additional stiffness to the second shaft section 30 at the interface between hypotube 20 and second shaft section 30 and along the length of stiffening member 50.

Stiffening member 50 is preferably formed from an elongated, thin stainless steel wire. Other materials having appropriate mechanical characteristics can of course be used. Stiffening member 50 provides additional stiffness to the second shaft section 30 in an amount that is a function of the cross sectional area of stiffening member 50 at a specific location of stiffening member 50. That is, a stiffening member having a nominal cross sectional area at a first location along its length will provide a first amount of stiffness at this location, while less stiffness will be provided at other selected locations along that length of the stiffening member having a reduced cross sectional area. To provide a varying amount of stiffness, then, stiffening member 50 thus preferably includes portions having a reduced cross sectional area as compared to the nominal cross sectional area of stiffening member 50.

Specifically, in the embodiment shown, stiffening member 50 includes a first region 51 having a constant cross sectional area along its length, and a tapered region 56 having reduced cross sectional area that changes along the length of tapered region 56. Tapered region 56 extends from a first location 53 of nominal cross sectional area to distal end 54 of stiffening member 50, which has a reduced cross sectional area that is less than the nominal cross sectional area. In the embodiment shown, the cross sectional area of stiffening member 50 decreases in a substantially linear manner along the length of tapered region 56 from first location 53 to distal end 54. In this manner, stiffening member 50 can be provided with a gradient of stiffness along the length of the tapered region 56, which in turn provides a gradient of additional stiffness to second shaft section 30 along the length of the tapered region 56 of the stiffening member 50. The reduced cross sectional area of tapered region 56 can be created by grinding down stiffening member along tapered region 56. Other methods for reducing the cross sectional area of stiffening member 50 along tapered region 56 can also be used.

While the cross sectional area of tapered region 56 is shown in FIGS. 1–3 as decreasing linearly along its length, the cross sectional area of tapered region 56 can vary in any manner desired, such as having a substantially constant reduced cross sectional area (as compared to the nominal cross sectional area) along the length of the tapered region, or having decreasing and increasing regions of cross sectional area along tapered region 56. In addition, stiffening member 50 can include any number of regions having reduced cross sectional area as compared to the nominal cross sectional area of stiffening member 50, as is desired.

Stiffening member 50 also preferably has a spherical member 57 at its distal end 54 that is greater than the cross sectional area of distal end 54. Because of its reduced cross sectional area, second shaft section 30 is susceptible to being punctured by distal end 54 as the second shaft section is advanced through a tortuous section of a patient's vasculature. Spherical member 57, or some other blunt member affixed to the distal end 54 of stiffening member 50, helps to prevent the distal tip 54 from puncturing second shaft section 30.

In the embodiment shown in FIGS. 1-3, the stiffening member 50 is fixedly attached to the distal end 24 of hypotube 20. The proximal end 52 of the stiffening member 50 is inserted into the lumen 26 at distal end 24 of hypotube 20, and is fixedly interconnected to the hypotube 20 through one or more crimps 48 (perhaps best shown in FIG. 3) formed in the hypotube 20. Crimps 48 can be evenly spaced about hypotube 24 if desired. Crimps 48 extend into the lumen 26 and contact the proximal end 52 of stiffening member 50. In this manner, a secure interconnection between the hypotube 20 and the stiffening member 50 is a created. Other mechanisms for fixedly interconnecting stiffening member 50 to hypotube 20, A such as adhesive or welding, can also be used. The fixed interconnection between stiffening member 50 and hypotube 20 creates a smoother stiffness gradient along the stiffening member 50, particularly through the tapered region 56 of the stiffening member 50. In addition, the overall profile of stiffening member 50 in such an embodiment remains the same as the bypotube 20, which can lead to more efficient use of catheter 10.

In this embodiment, the proximal end 52 of stiffening member 50 has the same cross sectional shape and area as lumen 26. As such, stiffening member 50 substantially occludes the lumen 26 of hypotube 20 at the distal end 24. To accommodate fluid flow through dilation catheter 10, a fluid port 28 is formed in the hypotube 20 to fluidly couple lumen 26 of hypotube 20 to lumen 36 of second shaft section 30. Fluid port 28 is formed at a location that is proximal of the fixed interconnection of proximal end 52 of stiffening member 54 to hypotube 20 at crimps 48. Fluid port 28 extends between lumen 26 and the exterior of the hypotube 20. As described above, the cross sectional area of lumen 36 of second shaft section 30 is greater than the cross sectional area of hypotube 20, and second shaft 30 overlaps a region that is adjacent the distal end 24 of hypotube 20. In particular, second shaft section 30 overlaps fluid port 28, and seal 38 is formed at a location that is proximal of fluid port 28. Fluid port 28 thus fluidly couples lumen 26 of hypotube 20 to lumen 36 of second shaft section 30 and defines a fluid pathway along dilation catheter 10.

FIG. 4 shows an alternative embodiment of the catheter structure for attaching a stiffening member 50' to a hypotube 20'. A portion of hypotube 20' is removed through a longitudinal, U-shaped cut that is made at the distal end 24' of hypotube 20'. Proximal end 52' (shown in phantom) of stiffening member 50' is inserted into hypotube 20'. The distal end 24' of hypotube 20' is then roll crimped about the proximal end 52' of stiffening member 50' to secure the stiffening member 50' to hypotube 20'. The roll crimp reduces the diameter of hypotube 20' in a region adjacent the distal end 24' of hypotube 20' to create a secure interconnection between stiffening member 50' and hypotube 20'. The length and depth of the longitudinal, U-shaped cut in hypotube 20' is of sufficient size so that when hypotube 20' is crimped about stiffening member 50', a fluid port 28' is formed in the hypotube 20'. Fluid port 28' is in fluid communication with a passage in a second shaft section of a dilation catheter in a manner similar to that described above.

FIG. 5 shows a third embodiment of a catheter structure in a hypotube 20" for attaching stiffening member 50" to its distal end 24". The structure of FIG. 5 is similar to that shown in FIG. 4 in that a longitudinal, U-shaped cut is made at distal end 24", and distal end 24" is roll crimped about stiffening member 50". The longitudinal, U-shaped cut in hypotube 20" is deeper than that of hypotube 20', however, so that the distal end 24" of hypotube 20" does not fully extend around the proximal end 52" of stiffening member 50". Solder 29 can be added at the top portion of hypotube 20" to secure stiffening member 50" to hypotube 20". The shape of the U-shaped cut is again such that, when hypotube 20" is crimped about stiffening member 50", a fluid port 28" is created in hypotube 20".

In a preferred embodiment, dilation catheter 10 has a total working length as measured from the proximal end 22 of the hypotube 20 to the tip 46 of the guide wire lumen 40 of approximately 59.25" (150.50 cm). The hypotube 20 is preferably formed from a length of stainless steel tube having a hollow diameter. The hypotube 20 is 45" (114.3 cm) in length, and the outer diameter of hypotube 20 is 0.025" (0.064 cm) while the inner diameter (i.e. the diameter of lumen 26) is 0.019" (0.048 cm).

The second shaft section 30 has a total length measured from its proximal end 32 to its distal end 34 of approximately 13.35" (33.91 cm). One material particularly well suited for second shaft section 30 is Nylon 12, which is commercially available in a variety of stiffnesses. Specifically, HYTREL® brand polymers, available from E. I. du Pont de Nemours, located in Wilmington, Del., and PEBAX® brand polymers, available from Elf Atochem in Philadelphia, Pa., are two families of polymers suitable for use in second shaft section 30. Second shaft section 30 can be formed from a single piece of tubing, and thus have a uniform stiffness along its length. Alternatively, and as shown in FIG. 1 and described above, second shaft section 30 can comprise a proximal portion 70 and a distal portion 72. Proximal portion 70 can be approximately 7" (17.78 cm) in length, and be formed from a section of 82 shore D durometer HYTREL® tubing, or from a section of 72 shore D durometer PEBAX® tubing. Distal portion 72 can be approximately 6.35" (16.13 cm) in length, and can be formed from 63 shore D durometer HYTREL® tubing, or from 63 shore D durometer PEBAX® tubing.

The guide wire lumen 40 of dilation catheter 10 preferably has a length of 8.25" (20.96 cm) as measured from skive 44 to the tip 46 at the distal end of the guide wire lumen 40. As described above, skive 44 preferably is positioned at the butt joint 74 between proximal portion 70 and distal portion 72 (i.e. approximately 7" (17.78 cm) from the proximal end 32 of second shaft section 30).

Seal 38 between second shaft section 30 and hypotube 20 is formed at the proximal end 32 of second shaft section 30, which extends over fluid port 28 of hypotube 20. More particularly, second shaft section 30 overlaps the region of hypotube 20 that is adjacent the distal end 24 by approximately 1" (2.54 cm). Seal 38 can thus be created proximal of fluid port 28 to fluidly couple lumen 26 and lumen 36.

Stiffening member 50 is preferably formed from a stainless steel wire having a circular cross sectional shape. Stiffening member 50 is approximately 7" (17.78 cm) long. The nominal diameter of stiffening member is within the range of 0.017" (0.043 cm) to 0.019" (0.048 cm). The proximal end 52 of stiffening member 50 extends into lumen 26 of hypotube 20 by approximately 0.1" (0.254 cm), and crimps 48 frictionally secure stiffening member 50 to hypotube 20. In a preferred embodiment, stiffening member includes a 2" (5.08 cm) region having a constant nominal diameter that extends from the proximal end 52 of stiffening member 50 (i.e. first region 51). Tapered region 56 of stiffening member 50 extends for approximately 5" (12.70 cm) from location 53 at the end of the constant diameter region to distal end 54 of stiffening member 50. First location 53 thus defines the interface between the constant diameter region and tapered region 56 of stiffening member 50. As such, first location 53 is preferably of nominal diameter. The tapered region 56 is ground down in a linear manner from first location 53 to distal end 54. Distal end 54 has a diameter of 0.003" (0.008 cm). The distal end 54 of stiffening member can include a spherical member 57 of material to prevent the stiffening member from puncturing the second shaft section 30 as the dilation catheter is advanced and navigated through a patient's vasculature. Spherical member 57 has a diameter of 0.008" (0.020 cm), and can be formed from the stainless steel wire from which stiffening member 50 is constructed from. Alternatively, spherical member 57 can be a separately formed member that is mounted to distal end 54 of stiffening member 50 using conventional methods, such as melting, adhesive, or solder.

The above described dimensions and materials for dilation catheter 10 are provided as an example of a preferred embodiment of the present invention. Other dimensions and materials of course can be used as desired for a specific application.

Dilation catheter 10 possesses many advantages over prior art dilation catheters. Specifically, the stiffening member 50 of dilation catheter 10 reduces the incidence of buckling and kinking along the length of the stiffening member 50 in the second shaft section 30. This is particularly advantageous at the interface between the hypotube 20 and the second shaft section 30, where the second shaft section previously had a tendency to "accordion" due to the axial loads placed on the catheter as the catheter was advanced along the guide wire. The first region 51, second region 55, and tapered region 56 preferably provide a smooth, gradual gradient of stiffness to the second shaft section 30, which helps to optimize the competing design criteria of dilation catheters. That is, the stiffening member 50 aids in pushability, without significantly decreasing the overall flexibility of the dilation catheter 10. Moreover, the flexibility profile of second shaft section 30 can be efficiently altered as desired by varying the geometry of stiffening member 50. Dilation catheter 10 is also efficient to manufacture and use as compared to prior art dilation catheters.

FIGS. 6 and 7 show dilation catheter 110 and dilation catheter 210, respectively, which are two alternative embodiments of the present invention. Dilation catheters 110 and 210 include many of the components of dilation catheter 10 shown in FIGS. 1–3 above and described above, and the description of those components are equally applicable to dilation catheters 110 and 210.

Hypotube 120 of dilation catheter 110 shown in FIG. 6 further includes an axial stop member 112, and stiffening member 150 of dilation catheter 110 is of the "floating" variety. That is, stiffening member 150 is free from fixed attachment to either the hypotube 120 or the second shaft section 130 of dilation catheter 110. Stiffening member 150 instead engages axial stop member 112 when the dilation catheter 110 is advanced in a body lumen.

Axial stop member 112 is comprised of a radial projection, such as a crimp 148, formed in hypotube 120 in a region adjacent the distal end 124 of hypotube 120. The proximal end 152 of stiffening member 150 engages the crimp 148 as the catheter 110 is advanced in a body lumen. Crimp 148 thus prevents further axial motion of stiffening member 150 in the proximal direction and positions stiffening member 150 to extend into second shaft section 130 to provide additional stiffness along its length. In the embodiment of FIG. 6, stiffening member 150 has a cross sectional shape and area that is substantially equal to the cross sectional shape and area of the lumen 126 of hypotube 120. In such an embodiment, a fluid port 128 is again provided in hypotube 120 between its distal end 124 and seal 138 to provide fluid communication between lumen 126 and lumen 136 of second shaft section 130. Other axial stops can of course be provided, such as a necked-down region of hypotube 120 that would create a frictional interface between the proximal end 152 of stiffening member 150 and the hypotube 120 to prevent further axial motion of stiffening member 150.

A guide wire lumen 140 is included within second shaft section 130. Guide wire lumen 140 terminates in a skive 144 to permit the insertion of a guide wire. In a catheter 110 having a floating stiffening member 150, skive 144 and guide wire lumen 140 also prevent stiffening member 150 from migrating into the distal portion of second shaft section 130. That is, guide wire lumen 140, skive 144, and stiffening member 150 are appropriately sized so as to create a restriction within second shaft section 130 that prevents migration of stiffening member 150.

Alternatively, as shown in FIG. 7, dilation catheter 210 can include a stiffening member 250 that defines a substantially linear fluid flow pathway through catheter 210. In this embodiment, stiffening member 250 has a cross sectional area that is less than the cross sectional area of lumen 226 of hypotube 220. Stiffening member 250 engages axial stop member 212 formed in hypotube 220 for preventing further axial motion of stiffening member 250. Because of the reduced cross sectional area of stiffening member 250 as compared to lumen 226, however, the fluid flow pathway through dilation catheter 210 is substantially linear between lumen 226 of hypotube 220 and lumen 236 of second shaft section 230 (i.e. through the distal end of the lumen 226 into lumen 236).

Although the present invention has been described with reference to preferred embodiments, those skilled in the art will recognize that changes may be made in the form and detail without departing from the spirit and scope of the invention. For example, the stiffening member of the present invention can extend along the length of the hypotube (or any portion thereof), and can have a variable cross sectional shape and area to provide flexibility in the manner in which the lumen of the first shaft section is fluidly coupled to the lumen of the second shaft section. Moreover, while only a rapid exchange catheter has been illustrated, the present invention is equally applicable to over-the-wire catheters, particularly in an embodiment where the stiffening member does not completely occlude the lumen of the first shaft section.

What is claimed is:

1. A dilation catheter for insertion into and advancement through a body lumen, the dilation catheter comprising:

a first shaft section having a proximal end, a distal end, and a first stiffness, the first shaft section further including a hollow passage along a length of the first shaft section for permitting fluid flow through the length of the first shaft section, and an axial stop member;

a second shaft section having a proximal end attached to a region adjacent the distal end of the first shaft section, a distal portion, and a second stiffness that is less than the first stiffness of the first shaft section, the second shaft section including a hollow passage along a length of the second shaft section that is in fluid communication with the hollow passage of the first shaft section;

a dilation member on the distal portion of the second shaft section and fluidly coupled to the hollow passage of the second shaft section to receive fluid;

a guide wire lumen in at least a portion of the second shaft section adapted to receive a guide wire; and a stiffening member in the hollow passage of the second shaft section, the stiffening member being free from fixed interconnection to the first shaft section, a proximal end of the stiffening member extending into the hollow passage of the first shaft section and engaging the axial stop member of the first shaft section to prevent axial motion of the stiffening member in the proximal direction beyond the axial stop member as the dilation catheter is inserted and advanced in the body lumen, the stiffening member for providing additional stiffness to the second shaft section of the dilation catheter at a region along the length of the stiffening member.

2. The dilation catheter of claim 1, wherein:

the proximal end of the stiffening member has a cross sectional shape and area that is substantially equal to the cross sectional shape and area of the hollow passageof the first shaft section at the distal end of the first shaft section to substantially occlude the hollow passage of the first shaft section when the stiffening member engages the axial stop member; and the first shaft section includes a fluid port proximal of the axial stop member, the hollow passage of the second shaft section being fluidly coupled to the fluid port to define a fluid pathway through the hollow passage and the fluid port ofthe first shaft section and the hollow passage of the second shaft section.

3. The dilation catheter of claim 2, wherein the axial stop member includes a crimp adjacent the distal end of the first shaft section, the crimp extending radially inward into the hollow passage of the first shaft section, the crimp being engaged by the proximal end of the stiffening member as the dilation catheter is advanced in a body lumen to prevent axial motion of the stiffening member beyond the crimp.

4. The dilation catheter of claim 2, wherein the stiffening member has a first cross sectional area at a first location of the stiffening member and a second cross sectional area at a second location of the stiffening member, the second cross sectional area being less than the first cross sectional area to define a tapered region between the first location and the second location, the tapered region having a gradient of stiffness along its length.

5. The dilation catheter of claim 4, wherein the stiffening member is a stainless steel wire having a cross sectional shape and area at its proximal end that is substantially equal to the cross sectional shape and area of the hollow passage of the first shaft section at the distal end of the first shaft section, the wire having ground reduced cross section portions along its length in the tapered region.

6. The dilation catheter of claim 1, wherein the proximal end of the stiffening member has a cross sectional area at its proximal end that is less than the cross sectional area of the hollow passage of the first shaft section at the distal end of the first shaft section to define a substantially linear fluid pathway between the hollow passage of the first shaft section and the hollow passage of the second shaft section.

* * * * *